(12) United States Patent
Scheirer et al.

(10) Patent No.: US 6,415,176 B1
(45) Date of Patent: Jul. 2, 2002

(54) SENSING AND DISPLAY OF SKIN CONDUCTIVITY

(75) Inventors: Jocelyn C. Scheirer, Somerville; Rosalind W. Picard, Newton, both of MA (US); Nancy Tilbury, London; Jonathan Farringdon, Kent, both of (GB)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/687,038

(22) Filed: Oct. 12, 2000

Related U.S. Application Data

(60) Provisional application No. 60/160,108, filed on Oct. 18, 1999.

(51) Int. Cl.[7] ................................................. A61B 5/05
(52) U.S. Cl. ........................................................ 600/547
(58) Field of Search .......................................... 600/547

(56) References Cited

U.S. PATENT DOCUMENTS

| 3,784,908 A | * | 1/1974 | Anderson ..................... 324/62 |
| 4,510,939 A | * | 4/1985 | Brenman et al. ............ 600/384 |
| 4,765,343 A | * | 8/1988 | Brenmen et al. ............ 600/384 |
| 5,897,505 A | | 4/1999 | Feinberg et al. ............ 600/547 |

* cited by examiner

*Primary Examiner*—Kevin Shaver
*Assistant Examiner*—Pamela Wingood
(74) *Attorney, Agent, or Firm*—Testa, Hurwitz & Thibeault, LLP

(57) ABSTRACT

A skin-conductivity sensor is configured as a wearable device, such as an article of clothing worn on the hand but covering it only partially. The device may include an on-board power source and a source of illumination that provides a continuous visual indication of skin conductivity.

7 Claims, 3 Drawing Sheets

SENSING AND DISPLAY OF SKIN CONDUCTIVITY

RELATED APPLICATION

This application claims the benefits of U.S. Provisional Application Ser. No. 60/160,108, filed on Oct. 18, 1999.

FIELD OF THE INVENTION

The present invention relates to physiological sensing, in particular to sensing and display of skin conductivity.

BACKGROUND OF THE INVENTION

The skin-conductivity response, also known as the electrodermal response, is the phenomenon whereby the skin momentarily becomes a better conductor of electricity in response to external or internal stimuli that are physiologically arousing. In this context, the term "arousal" broadly connotes overall activation—i.e., an increase in the intensity of general physiological activity. Arousal is widely considered one of the two main dimensions of an emotional response; the other, valence, represents the positive or negative quality of the response (so that winning an award is high arousal, positive valence whereas listening to a boring speech is low arousal, negative valence). Measuring arousal is therefore not the same as measuring emotion, but does capture an important component of it. Arousal has been found to be a strong predictor of attention and memory.

The stimuli to which skin conductivity is sensitive are manifold, including events of a novel, significant, or intense nature. Arousal level tends be low when a person is sleeping, and high in activated states such as rage or mental workload. Engaging in a task that imposes mental workload, such as solving math problems (even if not particularly difficult), will tend to cause skin conductivity to increase sharply and then gradually decline.

The skin-conductivity response is measured from the eccrine glands, which cover most of the body and are concentrated in the palms and the soles of the feet. The primary function of the eccrine glands is thermoregulation (by evaporative cooling of the body), which is related to aerobic activity. The eccrine glands located on the palmar and plantar surfaces, however, have been suggested to be more responsive to emotional and other significant stimuli. Emotion-evoked sweating, for example, is most evident in these areas due to the high gland density.

Conductivity is typically measured by placing two electrodes next to the skin and passing a minuscule electric current between the two points. When the subject experiences increased arousal, the skin immediately becomes a slightly better electrical conductor, and this response is detected by appropriate circuitry associated with the electrodes. Presently available devices, however, are elaborate and sophisticated, requiring specialized electrodes and gels, and are primarily intended for use in a laboratory setting. The measurement circuitry is ordinarily part of a stationary processing system.

DESCRIPTION OF THE INVENTION

Brief Summary of the Invention

The present invention provides a skin-conductivity sensor configured as a wearable device, preferably a glove (or, as shown in the figures, an article of clothing worn on the hand but covering it only partially). The device may include an on-board power source and processing hardware.

The design of the article is dictated, in part, by the locations of the conductivity-measuring electrodes. Electrodes in skin-conductivity sensors have traditionally been placed either on the middle phalanges of the digits (FIG. 1A) or on the bottom of the palmar surface of the hand (FIG. 1B). In accordance with the present invention, by contrast, a first electrode is held against the bottom of the palmar surface and a second electrode lies against the side of the hand, between the index finger and the thumb. This placement is particularly advantageous in facilitating configuration of a wearable skin-conductivity garment as a hand-worn article and in minimizing motion artifacts.

BRIEF DESCRIPTION OF THE DRAWINGS

The foregoing discussion will be understood more readily from the following detailed description of the invention, when taken in conjunction with the accompanying drawings, in which.

DETAILED DESCRIPTION OF THE PREFERRED EMBODIMENTS

Figure 1A:
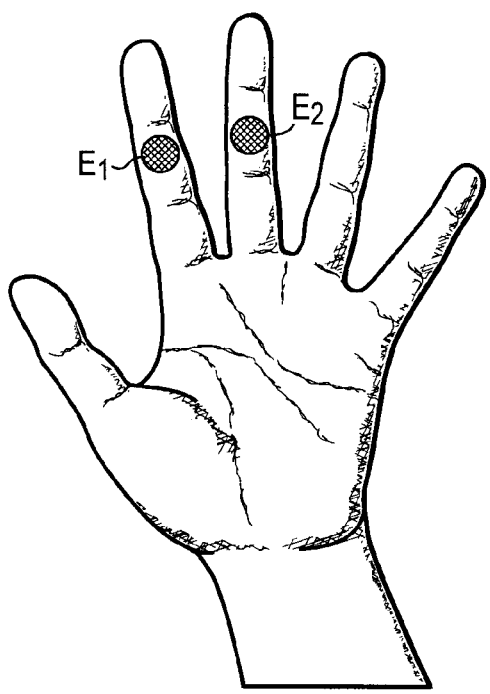
FIGS. 1A and 1B illustrate prior-art electrode placements for electrodermal sensors.
Figure 1B:
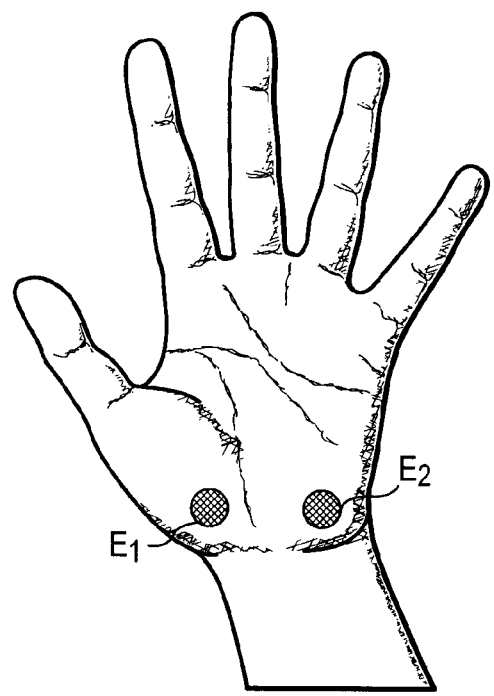
Figure 2:
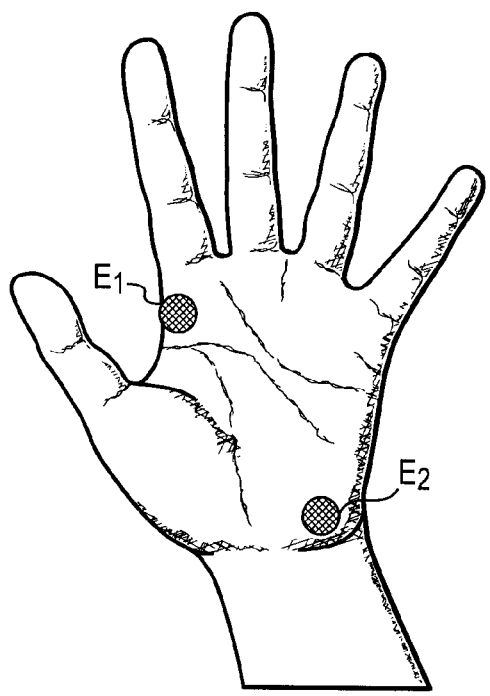
FIG. 2 illustrates sensor placement in accordance with the present invention.

In accordance with the present invention, and with reference to FIG. 2, a first electrode $E_1$ is held against the bottom of the palmar surface and a second electrode $E_2$ lies against the side of the hand, between the index finger and the thumb. This placement facilitates integration of the electrodes into a hand-worn article as illustrated in FIGS. 3A, 3B.

Figure 3A:
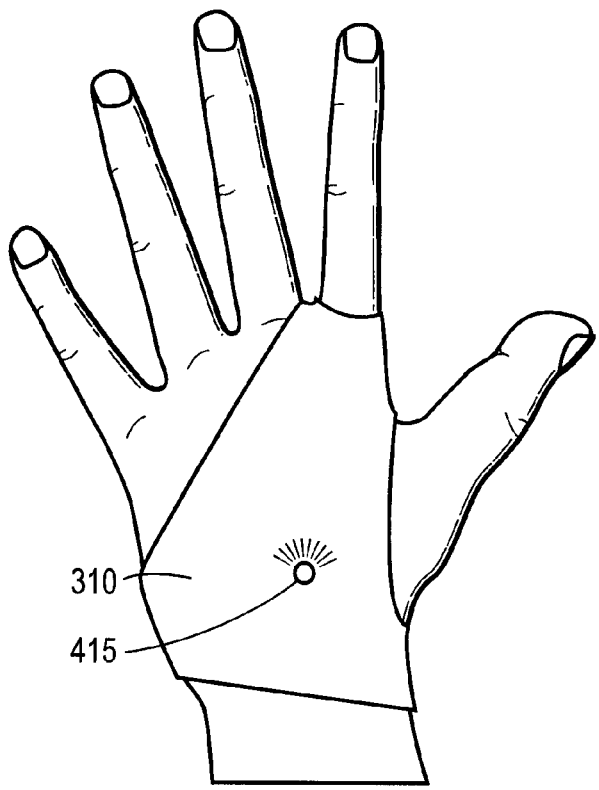
FIGS. 3A and 3B are front and back views of a wearable garment incorporating the sensors for placement as shown in FIG. 2.
Figure 3B:
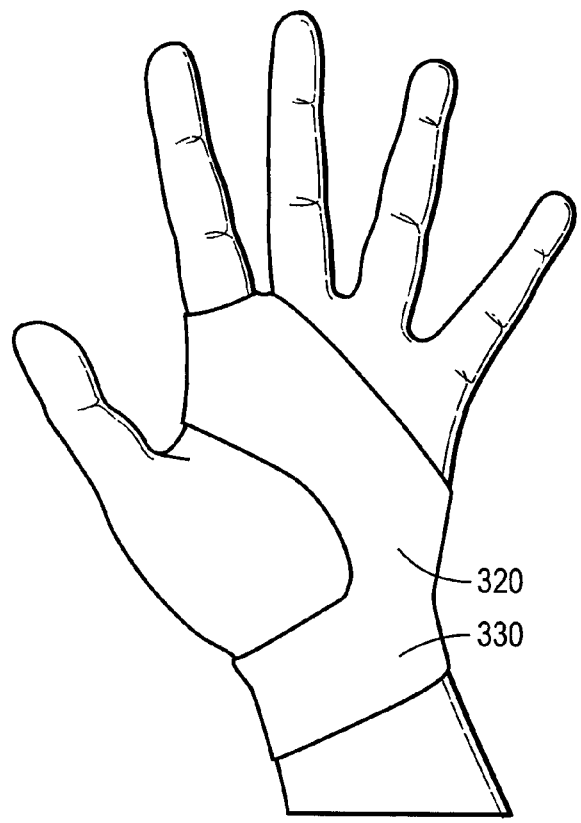

The article 300 shown in FIGS. 3A and 3B has a generally triangular rear panel 310. The front of the article 300 comprises a diagonal segment 320 extending from the wearer's index finger to a wristband segment 330. Segment 330 may be used to secure the article 300 to the wearer's hand, and may comprise, for example, complementary hook-and-pile (e.g., VELCRO) panels that are brought together across the wearer's wrist.

The configuration 300 is advantageous in that it does not cover any of the wearer's fingers and overlies the palm only partially; moreover, only two of the wearer's fingers are engaged at all (extending through separations between seams joining the panels). Because the article 300 does not mechanically affect the hand's normal range of motion, its use does not inconvenience the wearer, nor do hand motions interfere with sensing of skin conductivity. The various segments 310, 320, 330 may be fabricated from an elastic material, such as neoprene or nylon, and when worn as shown the article 300 allows for very stable signal generation. The article 300 presents a fashionable appearance, and may be worn as a supplement to normal clothing.

The electrodes $E_1$, $E_2$, which may be nickel-plated metal contacts, are affixed within diagonal segment 320 (behind the visible face of the segment) so as to be brought into contact with the inside of the wearer's hand at the positions shown in FIG. 2. The circuitry and readout of the invention, discussed below, can be contained within the rear panel 310.

Figure 4:
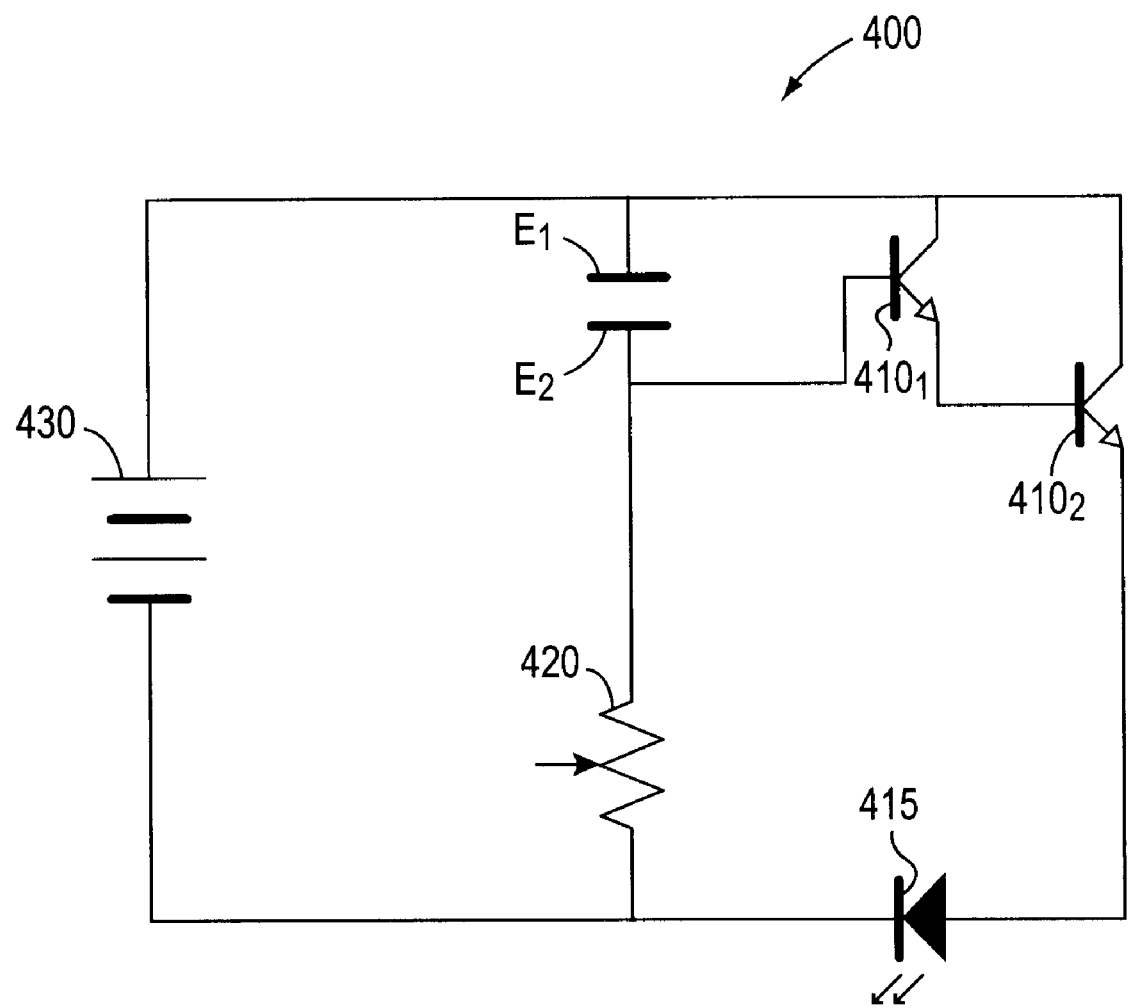
FIG. 4 is a representative circuit for operating the invention.

A preferred circuit is shown in FIG. 4. The illustrated circuit 400 contains a pair of NPN transistors $410_1$, $410_2$, which amplify the signal across the skin electrodes. Transistors $410_1$, $410_2$ operate a light-emitting diode (LED) so as to vary its output intensity in accordance with the amplified conductivity signal. In this way, the wearer as well as others can observe a visible indication of the signal and, hence, aspects of the wearer's physiological arousal and emotional state reflected in the electrodermal response. Indeed, LEDs visible at distances up to 50 feet, and requiring low power, are readily available (e.g., from LRI, Inc.).

A 500 kΩ potentiometer 420 determines the voltage drop across electrodes $E_1$, $E_2$, and therefore the voltage into transistor $410_1$ for a given skin-conductivity level. As a result, potentiometer 420 can be adjusted to accommodate the baseline conductivity of the individual wearer. While the average skin resistance ranges from 0.1–0.4 MΩ, different people exhibit varying baseline conductivity levels. By adjusting potentiometer 420 (which may be operated by a thumbwheel mounted on the rear panel 310 of the device, see FIG. 3A), the wearer can adjust for his or her baseline conductivity in order to maximize the device's response range.

Circuit 400, including two 3V watch batteries 430 that powers the circuit, may be contained within rear panel 310. As shown in FIG. 3A, the output of LED 415 may be mounted on (or visible from) the rear panel as well.

In operation, after adjustment to accommodate the wearer's baseline conductivity level, the observed brightness of LED 415 will indicate the wearer's degree of arousal. It is found, however, that individuals differ not only in terms of their baseline considered as an average over time, but also in terms of the signal variations contributing to the average. For some people, skin conductivity under non-stimulatory conditions varies little from the average, while others exhibit sharp signal peaks that depart considerably from the average. The former individuals are often referred to as "stabiles," while the latter are termed "labiles." Labiles using the present invention may observe more periodic LED brightness variations even if the device is properly adjusted for the time-averaged baseline skin-conductivity level.

Moreover, individual responses vary not only in terms of the baseline, but also in the degree and pattern of change from the baseline provoked by a given level of stimulation; that is, different people tend to respond differently to the same elicitation. For this reason, without knowledge of the individual's particular response pattern, the level of illumination cannot serve as an absolute indicator of arousal. It can, however, serve as an indicator of arousal patterns learned over time.

The output of transistor $410_2$ can of course be employed to drive devices other than an LED. For example, the galvanic skin response is commonly one of the physiological parameters measured by so-called lie detectors. The current that would otherwise drive LED 415 can instead be directed to an analytical apparatus or to drive a meter, chart recorder, data-capture device, A/D converter, real-time digitizer, etc. (e.g., by means of a jack on article 300 facilitating external electrical connection to circuitry 400).

Although the present invention has been described with reference to specific details, it is not intended that such details should be regarded as limitations upon the scope of the invention, except as and to the extent that they are included in the accompanying claims.

What is claim is:

1. A device for measuring skin conductivity, the device comprising:
   a. a wearable hand garment;
   b. a pair of electrodes associated with the garment, the garment holding the electrodes against the skin of the wearer's hand.
   c. associated with the garment, a circuit connected to the electrodes configured for measuring skin conductivity thereacross.

2. The device of claim 1 further comprising an illumination source associated with the garment and connected to the circuit, illumination from the source varying with the measured skin conductivity.

3. The device of claim 2 wherein the device has a rear panel adapted to be worn over the back of the wearer's hand, the illumination source comprising a light-emitting diode producing an output visible on the rear panel.

4. The device of claim 1 wherein the device has a rear panel adapted to be worn over the back of the wearer's hand, the circuit being contained within the rear panel.

5. The device of claim 1 wherein the garment is configured to hold a first of the electrodes against the bottom of the palmar surface of the wearer's hand and the other electrode against the upper palmar surface of the wearer's hand between the index finger and the thumb.

6. The device of claim 1 wherein the article does not cover any of the wearer's fingers and overlies only a portion of the palm of the wearer's hand, thereby not mechanically affecting a normal range of hand motion.

7. The device of claim 1 wherein the electrodes are placed so as to minimize motion artifacts.

* * * * *